United States Patent [19]
Ishima et al.

[11] Patent Number: 5,734,014
[45] Date of Patent: Mar. 31, 1998

[54] ELAFIN DERIVATIVE

[75] Inventors: Yoshiaki Ishima, Fujieda; Noriyuki Okawa, Ami-machi; Masaya Yoshida, Ami-machi; Sakae Amagaya, Ami-machi; Akira Kaji, Higashikurume, all of Japan

[73] Assignee: Tsumura & Co., Tokyo, Japan

[21] Appl. No.: 379,437

[22] PCT Filed: Aug. 11, 1992

[86] PCT No.: PCT/JP93/01133

§ 371 Date: Mar. 27, 1995

§ 102(e) Date: Mar. 27, 1995

[87] PCT Pub. No.: WO94/04697

PCT Pub. Date: Mar. 3, 1994

[30] Foreign Application Priority Data

Aug. 11, 1992 [JP] Japan .................................. 4-234085

[51] Int. Cl.$^6$ .................................................. C07K 7/00
[52] U.S. Cl. .................................................. 530/324
[58] Field of Search .................................. 530/324

[56] References Cited

U.S. PATENT DOCUMENTS 5,223,483  6/1993  Thomas et al. ........................ 514/12
5,464,822  11/1995  Christophers et al. ................. 514/12

FOREIGN PATENT DOCUMENTS 0402068  12/1990  European Pat. Off. .

OTHER PUBLICATIONS

Journal of Biological Chemistry, vol. 265, No. 25, pp. 14791–14795, Sep. 5, 1990, Oliver Wiedow, et al., "Elafin: an Elastase–Specific Inhibitor of Human Skin".

Proceedings of the National Academy of Sciences of USA, vol. 83, Sep. 1996, pp. 6692–6696, Robert C. Thompson, et al., "Isolation, Properties, and Complete Amino Acid Sequence of Human Secretory Leukocyte Protease Inhibitor, A Potent Inhibitor of Leukocyte Elastase".

Journal of Biological Chemistry, vol. 263, No. 15, pp. 7364–6369, May 25, 1988, Jan Potempa, et al., "An Elastase Inhibitor From Equine Leukocyte Cytosol Belongs to the Serpin Superfamily".

Biochemical and Biophysical Research Communications, vol. 166, No. 2, pp. 993–1000, Jan. 30, 1990, Mark S. Baker, et al., "Plasminogen Activator Inhibitor 2 (PAI-S) is not Inactivated by Exposure to Oxidants which can be Released from Activated Neutrophils".

Comp. Biochem. Physiol., vol. 98C, No. 2/3, pp. 359–367, 1991, Scott D. Patterson, et al., "The Tammar Wallaby Major Plasma Serpin: Partial Characterization Including the Sequence of the Reactive Site Region".

Medline, AN-88264939 & Thrombosis Research, vol. 49, No. 6, pp. 581–589, Mar. 15, 1988, T. Stief, et al., "Oxidative Inactivation of Purified Human Alpha–2–Antiplasmin, Antithrombin III and C1–Inhibitor".

Dayhoff, "Atlas of Protein Sequence and Structure, vol. 5, 1972, p. 96.

Schalkwijk et al., Biochim. Biophys. Acta 1096:148–154 (1991).

Wiedow et al., Elafin: An Elastase-specific Inhibitor of Human Skin, J. of Biol. Chem., vol. 265, No. 26, pp. 14,791–14,795, (1990).

Tsunemi et al., "Synthesis and Structure–Activity Relationships of Elatin . . . Biochem. and Biophys. Res. Com, vol. 185 No. 3, pp. 967–973, Jun. 30, 1992.

Saheki et al., "Primary Structure of the Human Elatin Precursor . . . Biochem. and Biophys Res. Com., vol. 185 No. 1, pp. 240–245, May 29, 1992.

Primary Examiner—Cecilia J. Tsang
Assistant Examiner—C. Delacroix-Muirheid
Attorney, Agent, or Firm—Oblon, Spivak, McClelland, Maier & Neustadt, P.C.

[57] ABSTRACT

Disclosed herein are elafin derivatives represented by an amino acid sequence of the following formula (I):

Ala–Gln–Glu–Pro–Val–Lys–Gly–Pro–Val–Ser–Thr–Lys–Pro–Gly–Ser– (I)
Cys–Pro–Ile–Ile–Leu–Ile–Arg–Cys–Ala–X–Leu–Asn–Pro–Pro–Asn–
Arg–Cys–Leu–Lys–Asp–Thr–Asp–Cys–Pro–Gly–Ile–Lys–Lys–Cys–Cys–
Glu–Gly–Ser–Cys–Gly–Met–Ala–Cys–Phe–Val–Pro–Gln wherein X represents leucine, isoleucine or valine, or represented by an amino acid sequence having homology to the first-mentioned amino acid sequence.

The elafin derivatives of the present invention are stable to oxidation compared with natural elafin so that they can be advantageously used as drugs such as an elastase inhibitors.

2 Claims, 4 Drawing Sheets

Natural elafin (reduced)

Natural elafin (activated)

ELAFIN DERIVATIVE

TECHNICAL FIELD

This invention relates to novel elafin derivatives, and more specifically to elafin derivatives resistant to oxidation and having similar elastase inhibiting activity to natural elafin.

BACKGROUND ART

By Wiedow et al., elafin has been isolated from psoriatics as a substance having elastase inhibiting activity and its amino acid sequence has been reported [J. Biol. Chem. 265, 14791(1990) and J. Biol. Chem. 266, 3356(1991); Japanese Patent Laid-Open No. 148299/1991]. Successful chemical synthesis of this elafin (hereinafter called "natural elafin") has also been reported (The 29th Peptide Chemistry Forum, 1991).

As a result of research by the present inventors, it has however been found that natural elafin is unstable to oxidation and its activity is significantly lowered by oxidation. In particular, elastase is secreted by neutrophils, and causes damage to tissue and at the same time, produces active oxygen in abundance. To use natural elafin as an elastase inhibitor, natural elafin is strongly desired to have stability to oxidation.

DISCLOSURE OF THE INVENTION

The present inventors have conducted extensive research with a view toward obtaining an elafin derivative stable to oxidation. As a result, it has been found that its stability to oxidation is improved by partly modifying the amino acid sequence of natural elafin, leading to the completion of the present invention.

The present invention therefore provides an elafin derivative represented by an amino acid sequence of the following formula (I) (SEQ ID NO:1):

Ala–Gln–Glu–Pro–Val–Lys–Gly–Pro–Val–Ser–Thr–Lys–Pro–Gly–Ser– (I)
Cys–Pro–Ile–Ile–Leu–Ile–Arg–Cys–Ala–X–Leu–Asn–Pro–Pro–Asn–
Arg–Cys–Leu–Lys–Asp–Thr–Asp–Cys–Pro–Gly–Ile–Lys–Lys–Cys–Cys–
Glu–Gly–Ser–Cys–Gly–Met–Ala–Cys–Phe–Val–Pro–Gln wherein X represents leucine, isoleucine or valine, or represented by an amino acid sequence having homology to the first-mentioned amino acid sequence.

BEST MODE FOR CARRYING OUT THE INVENTION

Figure 1:
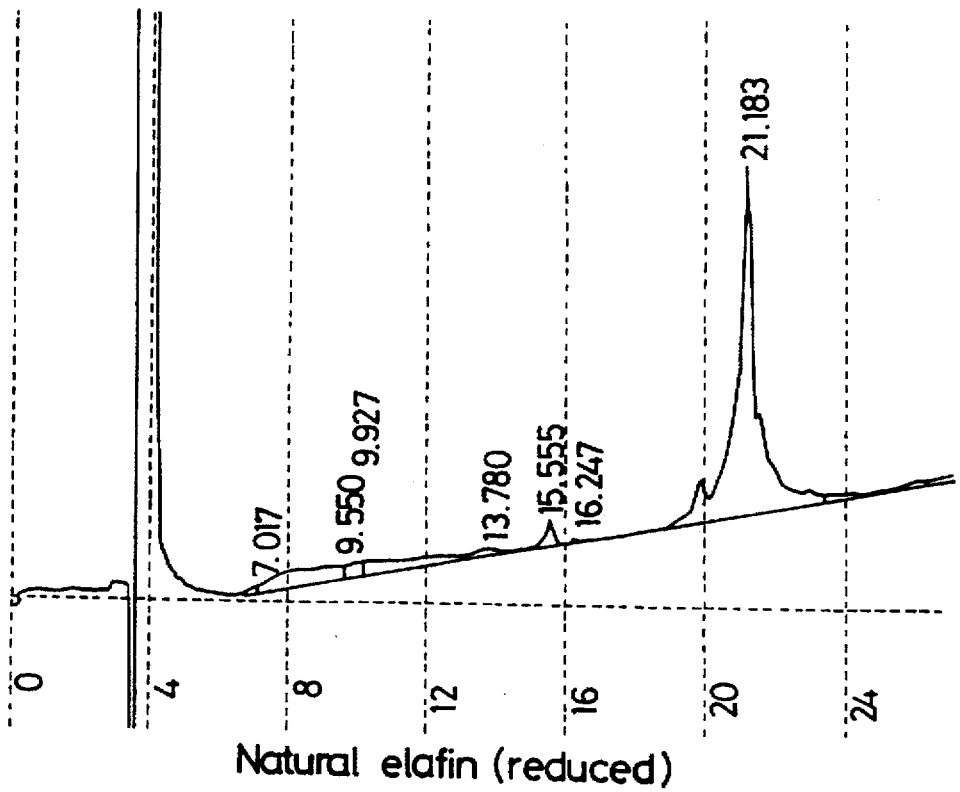
FIG. 1 is a diagram showing results of reverse phase HPLC of elafin in a reduced form and elafin in an activated form.
Figure 1:
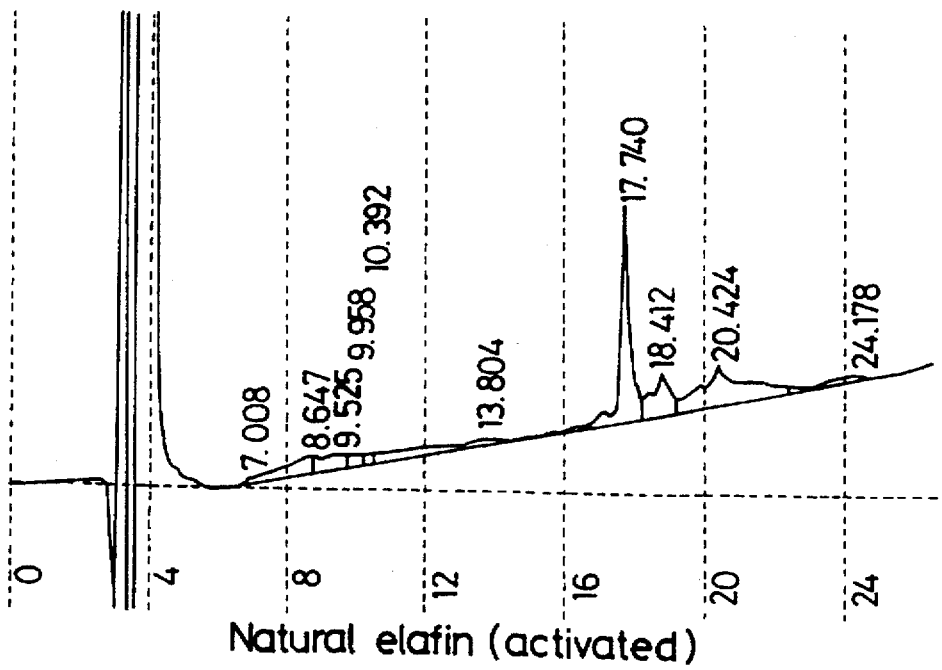

Although the elafin derivative according to the present invention may be chemically synthesized in accordance with the formula (I) by a known peptide synthesis process, it can be efficiently prepared by causing site-directed mutagenesis on a base, which codes a predetermined amino acid of a cloning vector in which a gene coding natural elafin has been incorporated, incorporating the thus-mutated gene or a gene of the elafin derivative, said gene having been separately prepared by chemical synthesis or the like, in an expression vector, and then culturing a host microorganism which has been transformed by the expression vector.

To prepare the elafin derivative according to the present invention by site-directed mutagenesis, it is first desired to conduct cloning of the gene of natural elafin.

Since a cloning method of natural elafin is known, the cloning can be conducted following this method (Japanese Patent Laid-Open No. 148299/1991 and the like).

Next, mutation is introduced into a base sequence (hereinafter called "the predetermined base sequence") of the resulting cloning vector, said predetermined base sequence corresponding to the 25th amino acid (methionine) of natural elafin.

Illustrative methods for the introduction of this mutation include a method in which the gene of natural elafin is partly removed by a restriction enzyme or the like and an oligonucleotide separately prepared by chemical synthesis is introduced into the removed part to obtain a cloning vector modified only in the predetermined base sequence (cassette mutagenesis) and a method in which the cloning vector modified only in the predetermined base sequence is obtained from a mutated oligonucleotide while using the gene of natural elafin as a template (site-directed mutagenesis).

The gene, which is useful as the template in the site-directed mutagenesis out of the methods described above, is a single-strand DNA or a double-strand DNA. Further, an elongating reaction of the gene useful as the template can be conducted using a DNA polymerass such as T4 DNA polymerase, Klenow fragment or Taq polymerase.

By the above-described methods, the predetermined base sequence can be converted from the base sequence coding methionine, which is weak against oxidation, to a base sequence coding an amino acid strong against oxidation, for example, leucine, valine, isoleucine or the like, thereby obtaining a cloning vector which contains a gene coding the elafin derivative of the present invention.

The cloning vector so obtained is introduced into the expression vector by a method known per se in the art. Furthermore, by culturing the host cells, which have been subjected to the target transformation with the expression vector, elafin derivatives according to the present invention can be expressed.

When the elafin derivative according to the present invention is prepared by genetic manipulation, no particular limitation is imposed on host cells to be used. *Escherichia coli*, yeast, *Bacillus subtilis*, animal cells or the like can be used.

As the cloning vector and the expression vector, known vectors suited to the kind of host cells can also be used.

Although the elafin derivative according to the present invention can be produced using various host cells as described above, it is particularly desired to produce it by using a yeast because a yeast can secrete the produced elafin derivative out of cells, its culturing time is short and no substantial cost is needed.

As a usable yeast, *Saccharomyces cerevisiae* can be mentioned. In particular, the BJ1991 strain, the BJ2168 strain, the 20B-12 strain or the like is preferred as host cells.

As a promoter for an expression vector when *Saccharomyces cerevisiae* is used, ADH2, ADH1, MFα1, GAP, GAL1, PHO1, PGK or the like is preferred. As a signal peptide for the expression of the elafin, a signal peptide of MFα1is preferred. Especially, an MFα1 signal peptide with a restriction enzyme EcoT14I site introduced therein by modification of the base sequence is preferred because it is convenient for construction.

Further, use of *Escherichia coli* as host cells also permit advantageous production of the elafin derivative according to the present invention. When *Escherichia coli* is used, the culturing time is shortest and no substantial cost is required. When producing the elafin derivative as a fusion protein, manipulations such as cutting of the fusion protein and conversion into an activated protein may be needed in some instances.

EXAMPLES

The present invention will next be described in further detail by the following examples, referential examples and tests. The present invention is however by no means limited by these examples.

Referential Example 1

Production of an Activated Elafin by *Escherichia coli*

(1) Synthesis of the elafin gene

The amino acid sequence of elafin, which is an elastase inhibitor, has been reported by O. Wiedow et al. [J. Biol. Chem. 265, 14791(1990) and J. Biol. Chem. 266, 3356 (1991)]. This is indicated by the following formula (SEQ ID NO:2):

Ala-Gln-Glu-Pro-Val-Lys-Gly-Pro-Val-Ser-Thr-Lys-Pro-Gly-Ser-
Cys-Pro-Ile-Ile-Leu-Ile-Arg-Cys-Ala-Met-Leu-Asn-Pro-Pro-
Asn-Arg-Cys-Leu-Lys-Asp-Thr-Asp-Cys-Pro-Gly-Ile-Lys-Lys-
Cys-Cys-Glu-Gly-Ser-Cys-Gly-Met-Ala-Cys-Phe-Val-Pra-Gln

Based on this amino acid sequence, the elafin gene was prepared. By adding the codon of tryptophan to a side of the N-terminal of the N-terminal amino acid, alanine, of elafin, the above gene was designed so that the cutting from the fusion protein can be achieved by a chemical method with N-bromosuccinimide (NBS) or 2-(2-nitrophenylsulfenyl)-3-methyl-3-bromo-indole (BNPS-skatole) or by enzymatic partial hydrolysis with chymotrypsin. Further, EcoRI-Hind III sites were introduced to opposite ends of the gene, respectively.

After having been chemically synthesized by a DNA synthesizer ("Model 380B"; manufactured by ABI Inc.) and then deprotected, an oligonucleotide was purified by reverse phase HPLC or polycrylamide electro-phoresis.

After the oligonucleotide was phosphorylated with T4-DNA kinase, it was subjected to ligation with T4-DNA ligase. Subsequent to further treatment of the reaction product with EcoRI-Hind III. a band of a target size (185 bp) was purified by electrophoresis through 4% low m.p. agarose.

The DNA fragment was ligated with an EcoRI-Hind III fragment of plasmid pTZ18R by T4-DNA ligase so that plasmid pTZ-EN107 was prepared. The elafin gene was confirmed by checking its base sequence with a DNA sequencer ("Model 373A"; manufactured by ABI Inc.).

(2) Preparation of a recombinant of *Escherichia coli*

(a) Preparation of pGEN1 and pGENH1.

Plasmids pGM1,pGMH1 were constructed based on the commercial plasmid pDR720 (product of Pharmacia AB). These plasmids have the gene of galK266 amino acid downstream the tryptophan promoter and their Mlu sites have been converted to EcoRI-Hind III sites, respectively, so that desired genes can be introduced into the EcoRI-Hind III sites, respectively. This makes it possible to express fusion proteins with a galK protein. PGM1 is a plasmid of the pBR series, while pGM1 is a plasmid of the pUC series.

This plasmid pGM1 was digested with EcoRI-Hind III and isolated by electrophoresis through 0.7% low m.p. agarose, whereby a band of approximately 4.1 kbp was cut out. This gel fragment was heated and dissolved at 65° C. for 5 minutes. Phenol was added, followed by stirring. An upper layer obtained subsequent to centrifugation was stirred further with phenol-chloroform and chloroform, each followed by centrifugation. An upper layer was added with 1/10 volume of 3M sodium acetate and 2.5 volumes of ethanol. By ethanol precipitation, the target pGM1 (EcoRI-Hind III) fragment was obtained.

(b) On the other hand, the plasmid pTZ-EN107 obtained above in (1) was digested with EcoRI-Hind III and isolated by electrophoresis through 2% low m.p. agarose, whereby a band of approximately 185 bp was cut out. This gel fragment was heated and dissolved at 65° C. for 5 minutes. Phenol was added, followed by stirring. After centrifugation, an upper layer was stirred further with phenol-chloroform and chloroform, each followed by centrifugation. An upper layer obtained by the centrifugation was added with 1/10 volume of 3M sodium acetate and 2.5 volumes of ethanol. ethanol precipitation, the target elafin gene (EcoRI-Hind III) fragment was obtained.

(c) The pGM1 (EcoRI-Hind III) fragment and the elafin gene (EcoRI-Hind III) fragment were subjected to ligation with T4-DNA ligase. Using this reaction mixture, an *Escherichia coli* strain C600galK⁻ was transformed by the Hanahan's method so that the target transformant pGEN1/C600galK⁻ was prepared. Confirmation of the plasmid was conducted based on a fragment pattern obtained by cutting the transformant with restriction enzymes.

Using the plasmid pGMH1, a transformant pGENH 1/C600galK⁻ was prepared by similar procedures.

(3) culture of the *Escherichia coli* strain and expression of a fusion protein

The recombinant pGENH1/C600galK⁻ obtained above in (2) was cultured at 30° C. overnight in L-medium which contained 100 µg/ml of ampicillin and 100 µg/ml of tryptophan. One milliliter of the culture was cultured further at 30° C. for 2.5 hours in 200 ml of L-medium which contained 100 µg/ml of ampicillin and 100 µg/ml of tryptophan. 2.5 hours later, the culturing temperature was raised to 37° C., at which the culturing was continued overnight. Expression of the plasmid pGENH1 was induced by shifting the temperature from 30° C. to 37° C.

The culture was centrifuged (6000 rpm, 10 minutes, 4° C.) and the cells so collected were ultrasonically disrupted. The suspension so obtained was centrifuged (15000 rpm, 30 minutes, 4° C.) so that the suspension was separated into a soluble fraction and an insoluble fraction.

Each fraction was subjected to SDS-PAGE by the Laemmli's method, followed by staining with CBB (Coomassie Brilliant Blue R-250). A band having a molecular weight of approximately 36000 was then detected on the cultured cells. This band was also confirmed to be an insoluble fraction. This protein was estimated to be a fusion protein of galK (266 residual groups) and elafin (57 residual groups).

(4) Cutting of the fusion protein

After the insoluble fraction having a wet weight of 700 mg was solubilized with 6 ml of 6M guanidine hydrochloride, the resulting solution was diluted with a phosphate buffer (the final concentration: 2M guanidine hydrochloride; 100 mM phosphate (pH 7) buffer). The diluted solution was centrifuged (15000 rpm, 30 minutes, 20° C.). The soluble fraction was added with 1.2 mg of chymotrypsin (product of WAKO PURE CHEMICAL INDUSTRIES, LTD.), followed by reaction at 37° C. for 30 minutes. The solution was added with 3 ml of 1M dithiothreitol and 44 ml of 6M guanidine hydrochloride, followed by incubation at 65° C. for 2.5 hours so that the protein was completely reduced.

A portion of the reaction mixture was analyzed by reverse phase HPLC. Through a comparison with analysis results obtained by processing the galK fusion protein other than elafin in a similar manner, a peak specific to the galk[31] elafin fusion protein was detected. This peak was collected by fractionation and then analyzed by a peptide sequencer ("477A"; manufactured by ABI Inc.). The sequence from the N-terminal of elafin was confirmed. In purification procedures to be described subsequently, the position of elusion of this peak in reverse phase HPLC was used as an index.

(5) Purification of reduced elafin

The solution was loaded on a reverse phase column ("C18", 1.6×12 cm; product of YMC). After the column was washed with 20% acetonitrile, elution was conducted with 60% acetonitrile, followed by desalting.

The eluate was concentrated and then loaded on a cation exchange column ("S-Sepharose FF", 1.6×12 cm; product of Pharmacia AB). After the column was washed with a phosphate buffer [40 mM phosphate buffer (pH 6.5), 10 mM dithiothreitol], elution was conducted with a buffer containing 1M NaCl.

The eluate was purified by reverse phase HPLC ("YMC-AM312").

The resulting sample was analyzed by the peptide sequencer ("477A", manufactured by ABI Inc.) so that the sequence from the N-terminal of elafin was confirmed. In addition, peaks which were presumed to be 259Pro- and 12Ala- as fragments of the galK protein were also observed as minor peaks. This sample was estimated to have MW 6006.8 as a result of mass spectroscopy by FAB-MASS. This molecular weight is consistent with the molecular weight of elafin in the reduced form.

(6) Preparation of activated elafin

The reduced elafin purified as described above was left over at a concentration of 0.1 mg/ml in 0.1M tris-hydrochloric acid buffer (pH 8.5) at room temperature for 22 hours. The solution was added with 1/20 volume of 10% acetic acid and then analyzed by the reverse phase HPLC ("YMC-AM312). A main peak was eluted earlier than that of reduced elafin (FIG. 1).

The main peak was purified, and its elastase inhibiting activity was measured. It exhibited strong inhibiting activity. Reduced elafin, however, did not show any inhibiting activity. This activated elafin was estimated to have MW 6000.9 as a result of mass spectroscopy by FAB-MASS. When this activated elafin was reduced by dithiothreitol, the eluted position by reverse phase HPLC shifted to the same position as reduced elafin. As a consequence, activated elafin was estimated to form S—S bonds of cysteine in the molecule of elafin.

Referential Example 2

Production of activated elafin by yeast:

Using the elafin gene obtained above in Referential Example 1(1), an enzymatic elafin secretory expressing vector was constructed by procedures to be described below.

(1) Preparation of a recombinant (a) Preparation of pMFα8/ADH2p

A plasmid pMFα8/ADH2p was prepared by obtaining an ADH2 promoter region, which was reported by D. W. Russell in J. Biol. Chem. 258, 2674–2682, 1983, in accordance with a polymerase chain reaction and substituting it for the MFα1-promoter region of plasmid pMFα8 (ATCC 37418).

(b) Preparation of pAMdB18R

A plasmid pAMdB18R was prepared by introducing the ADH2 promoter and MFα1-prepro region of the plasmid pMFα8/ADH2p into the plasmid pTZ18R.

(c) Preparation of pAMET18R

A protected oligonucleotide corresponding to an oligonucleotide (5'-TTTTATCCAAGGATACCCCTT (SEQ ID NO:9)) was chemically synthesized by the DNA synthesizer ("Model 380B"; manufactured by ABI Inc.). After the protected oligonucleotide was deprotected, purified by polyacrylamide electrophoresis and phosphorylated by using T4-DNA kinass, whereby the oligonucleotide (5'-pTTTTATCCAAGGATACCCCTT (SEQ ID NO:9)) was prepared.

Using the above-described plasmid pAMdB18R and the above-described oligonucleotide, site-directed mutagenesis was conducted in accordance with the Manual of "Mutan-K" (product of TAKARA SHUZO CO., LTD.), whereby the restriction enzyme EcoT14I site was introduced into the MFα1-prepro region to obtain pAMET18R. The introduction of EcoT14I site in the plasmid pAMET18R was confirmed based on a fragment pattern obtained by digestion with restriction enzymes.

(d) Preparation of pAMELF18R

The above-described plasmid pAMET18R was treated with EcoT14I-StuI. The reaction mixture was isolated by electrophoresis through 0.7% low m.p. agarose, whereby a band of approximately 4.3 kbp was cut out. This gel fragment was heated and dissolved at 65° C. for 5 minutes. The solution was added with phenol and then centrifuged. The upper layer obtained by the centrifugation was stirred further with phenol-chloroform and chloroform, each followed by centrifugation. An upper layer obtained by the centrifugation was added with 1/10 volume of 3M sodium acetate and 2.5 volumes of ethanol. By ethanol precipitation, the target pAMET18R9EcoT14I-Blunt) fragment was obtained.

On the other hand, the elafin gene obtained in Referential Example 1(1) was converted to have a blunt end by using Klenow fragment. After being digested with AvaII, the reaction mixture was isolated by electrophoresis through 2.5% low m.p. agerose so that a band of approximately 163 bp was cut out. The gel fragment was heated and dissolved at 65° C. for 5 minutes. The solution was added with phenol and then centrifuged. The upper layer was stirred further with phenol-chloroform and chloroform, each followed by centrifugation. An upper layer obtained by the centrifugation was added with 1/10 volume of 3M sodium acetate and 2.5 volumes of ethanol. By ethanol precipitation, the target elafin gene (AvaII-Blunt) fragment was obtained.

(e) A protected oligopeptide corresponding to the DNA fragment coding a portion of MFα1 signal peptide and the N-terminal region of elafin was chemically synthesized by the DNA synthesizer ("Model 380B"; manufactured by ABI Inc.). After the protected oligopeptide was deprotected, purified by polyacrylamide electrophoresis and phosphorylated by using T4-DNA kinase, whereby DNA fragments (EcoT14I-AvaII, 5'-pCTTGGATAAAAGGGCACAGGAACCAGTTAAAG (SEQ ID NO:10), 5'-pGACCTTTAACTGGTTCCTGTGCCCTTTATC SEQ ID NO:11)) were obtained.

The pAMET18R (EcoT14I-Blunt) fragment, the elafin gene (AvaII-Blunt) fragment and the DNA fragment (EcoT14I-AvaII) were subjected to ligation with T4-DNA ligase. Using this reaction mixture, the *Escherichia coil* NM522 was transformed by a method known per se in the art, that is, by the Hanahan's method so that the target transformant pAMELF18R/NM522 was obtained. The insertion of the gene was confirmed by digestion with restriction enzymes. The base sequence of the elafin gene was confirmed by the DNA sequencer ("Model 373A"; manufactured by ABI Inc.).

(f) Preparation of pELFMFAα8

The plasmid pMFα8/ADH2p was treated with BamHI-StuI. The reaction mixture was isolated by electrophoresis through 0.7% low m.p. agarose, whereby a band of approximately 5.4 kbp was cut out. This gel fragment was heated and dissolved at 65° C. for 5 minutes. The solution was added with phenol and then centrifuged. The upper layer after the centrifugation was stirred further with phenol-chloroform and chloroform, each followed by centrifugation. The resulting upper layer was added with 1/10 volume of 3M sodium acetate and 2.5 volumes of ethanol. By ethanol precipitation, the target pMFα8/ADH2p(BamHI-Blunt) fragment was obtained.

The plasmid pAMELF18R obtained above in (d) was treated with EcoRI and then converted to have a blunt end by using Klenow fragment. Subsequent to further treatment with BamHI, the reaction mixture was isolated by electrophoresis through 0.7% low m.p. agerose so that a band of approximately 1.7 kbp was cut out. The gel fragment was heated and dissolved at 65° C. for 5 minutes. The solution was added with phenol and then centrifuged. The upper layer subsequent to the centrifugation was stirred further with phenol-chloroform and chloroform, each followed by centrifugation. The resulting upper layer was added with 1/10 volume of 3M sodium acetate and 2.5 volumes of ethanol. By ethanol precipitation, the target pAMELF18R(BamHI-Blunt) fragment was obtained.

The pMFα8/ADH2p(BamHI-Blunt) fragment and the pAMELF18R(BamHI-Blunt) fragment were subjected to ligation with T4-DNA ligase. Using this reaction mixture, the *Escherichia coli* strain NM522 was transformed by a method known per se in the art, that is, by the Hanahan's method so that the target transformant pELFMFAα8/NMS522 was prepared. The confirmation of the plasmid was conducted fragments obtained by digestion with restriction enzymes.

(2) Transformation of yeast

Using the plasmid pELFMFAα8, the yeast BJ1991 strain (YEAST GENETIC STOCK CENTER) was transformed in accordance with the KUR[s method ["Cell Technology and Breeding of Yeasts", compiled by Susumu Nagai (1986)]. The resulting pELFMFAα8/BJ1991 was cultured at 30° C. for 2 days in 100 ml of YNB/CAA medium* which were placed in a 500 ml Erlenmeyer flask. The culture was centrifuged (3000 rpm, 5 minutes, 20° C.) and the resulting precipitate was suspended in 8.2 ml of YEPD medium**. In a 500 ml Erlenmeyer flask, 2 ml of the suspension (OD550= 1.5) was added to 100 ml of YEPD medium, followed by culturing at 30° C. for 2 days.

*YNB/CAA medium:

| Yeast nitrogen base w/o amino acids | 6.7 g |
|---|---|
| Glucose | 10 g |
| Casamino acid | 5 g |
| Adenine sulfate | 20 mg |
| Uracil | 20 mg |
| | 1 l |

**YEPD medium:

| Yeast extract | 10 g |
|---|---|
| Peptone | 20 g |
| Glucose | 20 g |
| Adenine sulfate | 20 mg |
| Uracil | 20 mg |
| | 1 l |

(3) Purification of activated elafin

The above-described culture was centrifuged (8000 rpm, 10 minutes, 4° C.) and the supernatant was filtered (0.22 um, Falcon Company). After the filtrate was subjected to ultrafiltration ("YM2 Membrane", cut at MW 1000; product of Amicon Corporation), the residue was purified by chromatography on a cation exchange column ("S-Sepharose FF", 1.6×12 cm; product of Pharmacia AB; 40 mM phosphate buffer (pH 6.5), NaCl 0–0.5 M gradient).

An active fraction so eluded was purified by reverse phase HPLC ("YMC-AM312").

The sample so obtained was detected at the same eluted position by reverse phase HPLC as activated elafin produced by *Escherichia coli* and showed similar elastase inhibiting activity to the latter. An analysis by the peptide sequencer ("477A"; manufactured by ABI Inc.) confirmed the sequence from the N-terminal of elafin. As a result of mass spectroscopy by FAB-MASS, the sample was estimated to have MW 5999.4. This molecular weight was consistent with that of active elafin produced by *Escherichia coli*.

Example 1

Production of elafin derivative

Figure 2:
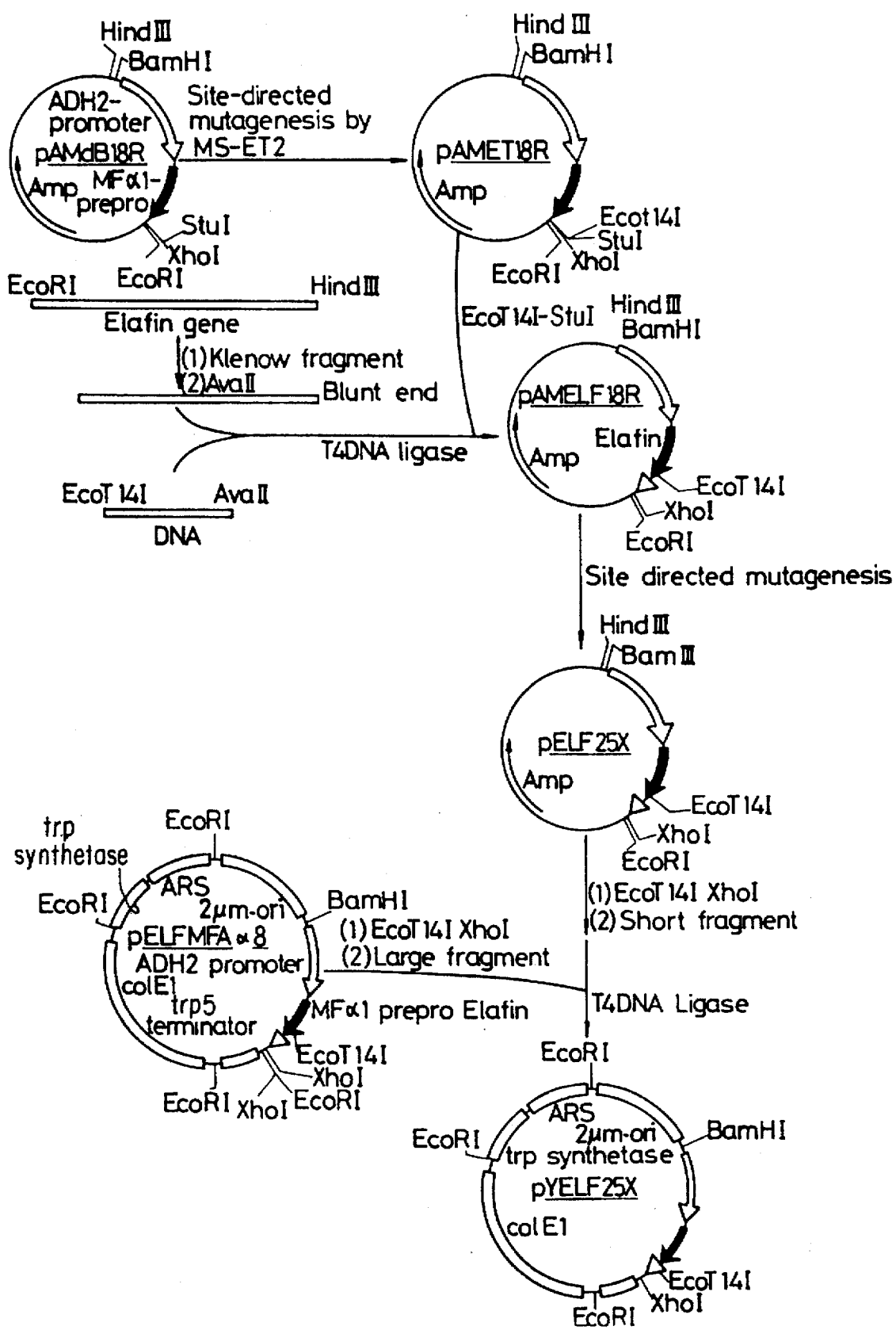
FIG. 2 is a diagram depicting the construction of a vector capable of expressing an elafin according to the present invention.

By the procedures shown in FIG. 2, the elafin gene of the plasmid PAMELF18R was modified through site-directed mutagenesis so that an elafin derivative was produced.

(1) Modification of the base sequence corresponding to the 25th mutagenesis from the N-terminal of the natural elafin gene (a) Preparation of pELF25x (x=L, I or V)

Three kinds of oligonucleotides IE-1,VE-1,LE-1 were obtained by chemically synthesizing their corresponding protected oligonucleotides with the DNA synthesizer ("Model 380B"; manufactured by ABI Inc.) and, after their deprotection, conducting purification in accordance with polyacrylamide electrophoresis.

IE-1:

5'-CGGGTTCAGAATAGCGCAGCG (SEQ ID NO:12)

VE-1:

5'CGGGTTCAGGACAGCGCAGCG (SEQ ID NO:13)

LE-1:

5'-CGGGTTCAGCAAAGCGCAGCG (SEQ ID NO:14)

Using the three kinds of oligonucleotides so obtained, site-directed mutagenesis of pAMELF18R was conducted in accordance with the Manual of "Mutan-K"(product of TAKARA SHUZO CO., LTD.) as will be described below, whereby three kinds of plasmids pELF25x (x=L, I or V) having the genes of three kinds of elafin derivatives were prepared.

Namely, using the plasmid pAMELF18R, *Escherichia coli* strain BW313 (F',dut⁻,ung⁻) was transformed by a method known per se in the art, that is, by the Hanahan's method so that the target transformant pAMELF18R/ BW313 was prepared. The transformant pAMELF18R/ BW313 was cultured in 2xYT medium (ampicillin 100 µg/ml) and in a manner known per se, a phage (M13K07) was added to cause infection (37° C., 1 hour). A portion of the culture was cultured overnight in 2xYT medium (kanamycin 100 µg/ml).

The culture (1.2 ml) was centrifuged (16000 rpm, 10 minutes) to obtain 1 ml of a culture supernatant, to which 200 µl of 20% PEG solution (3.5M sodium chloride, 20% polyethylene glycol 6000) were added. The resulting mixture was left over at room temperature for 30 minutes. After the solution was centrifuged (16000 rpm, 10 minutes), the precipitated phage was dissolved in 100 µl of LT buffer (10 mM tris-hydrochloric acid (pH 7.5), 0.1 mM EDTA). The solution was added with the same volume of phenol. The mixture so obtained was stirred and then left over for 5 minutes. After the mixture was centrifuged (15000 rpm, 2 minutes), the upper layer was collected and was added with 1/10 volume of 3M sodium acetate and 2.5 volumes of ethanol. By ethanol precipitation, the target single-stranded DNA in which the thymine of pAMELF18R had been replaced to uracil was obtained.

0.2 pmole of the single-stranded DNA so obtained was dissolved in 10 µl of an annealing buffer [20 mM tris-hydrochloric acid (pH 8.0), 10 mM magnesium chloride, 50 mM sodium chloride, 10 mM dithiothreitol]. 2-µl portions of the solution were added with the oligonucleotide solutions of the 5'-phosphorylated IE-1, VE-1 and LE-1 in the same volume, respectively. The solutions contained the respective oligonucleotides in 2 pmoles. The resultant mixtures were each heated at 65° C. for 10 minutes and then cooled gradually.

Each mixture (2 µl) was added with 25 µl of an extension buffer [50 mM tris-hydrochloric acid (pH 8.0), 60 mM ammonium acetate, 5 mM magnesium chloride, 5 mM dithiothreitol, 1 mM nicotinamide adenine dinucleotide, 0.5 mM dNTP). Further, 60 units of *Escherichia coli* DNA ligase and 1 unit of T4 DNA polymerase were added, followed by reaction at 25° C. for 2 hours.

This reaction mixture (3 µl) and 30 µl of BMH71-18 mutS competent cells were mixed, followed by incubation at 0° C. for 30 minutes and then at 42° C. for 90 seconds. After the mixture so obtained was left over, 300 µl of SOC medium were added, followed by shaking at 37° C. for 1 hour. The resulting mixture was added with 10µl of the phage solution. The mixture so obtained was left over to cause infection. Further, 2 ml of 2xYT medium (kanamycin 100 µg/ml, ampicillin 100 µg/ml) were added, followed by overnight culturing at 37° C.

The culture was centrifuged (15000 rpm, 10 minutes) so that the culture supernatant was obtained as a phage solution. This phage solution (20 µl) was mixed with 80 µl of NM522 cell culture solution. The mixture so obtained was left over to cause infection. A portion of the mixture was spread over an LB (ampicillin 100 µg/ml) plate, whereby a clone including plasmid pELF25x (x=L, I or V) which has been subjected to site-directed mutagenesis was obtained.

The base sequence of the gene which had been subjected to site-directed mutagenesis was confirmed using the DNA sequencer ("Model 373A"; manufactured by ABI Inc.).

The plasmid pELF25x (x=L, I or V) was confirmed to contain an elafin derivative gene in which the 25th residual group from the N-terminal of elafin, methionine, had been changed to leucine (L), isoleucine (I) or valine (V).

(b) Preparation of pYELF25x (x=L, I or V)

The plasmid pELF25L obtained above in (1) was digested with XhoI-EcoT14I. The reaction mixture was isolated by electrophoresis through 0.7% low m.p. agarose, whereby a band of approximately 196 bp was cut out. This gel fragment was heated and dissolved at 65° C. for 5 minutes. The solution was added with phenol. The resulting mixture was stirred and then centrifuged. The upper layer after the centrifugation was stirred further with phenol-chloroform and chloroform, each followed by centrifugation. The resulting upper layer was added with 1/10 volume of 3M sodium acetate and 2.5 volumes of ethanol. By ethanol precipitation, the target pELF25L(XhoI-EcoT14I) fragment was obtained.

On the other hand, the plasmid pELFMFAα8 was digested with XHoI-EcoT14I. The reaction mixture was isolated by electrophoresis through 0.7% low m.p. agarose so that a band of approximately 6.9 kbp was cut out. The gel fragment was heated and dissolved at 65° C. for 5 minutes. The solution was added with phenol. The resulting mixture was stirred and then centrifuged. The upper layer subsequent to the centrifugation was starred further with phenol-chloroform and chloroform, each followed by centrifugation. The upper layer obtained by the centrifugation was added with 1/10 volume of 3M sodium acetate and 2.5 volumes of ethanol. By ethanol precipitation, the target pELFMFAα8(XhoI-EcoT14I) fragment was obtained.

The pELF25L(XhoI-EcoT14I) fragment and the pELFMFAα8(XhoI-EcoT14I) fragment were subjected to ligation with T4-DNA ligase. Using this reaction mixture, the *Escherichia coli* strain NM522 was transformed by a method known per se in the art, that is, by the Hanahan's method so that the target transformant pYELF25L/NM522 was prepared. The confirmation of the plasmid was conducted based on a fragment pattern determined by digestion with restriction enzymes. In a similar manner, pYELF25I and pYELF25V were obtained.

(2) Transformation of yeast

Using the plasmid pYELF25L, the yeast BJ1991 strain (YEAST GENETIC STOCK CENTER) was transformed in accordance with the KUR's method ["Cell Technology and Breeding of Yeasts", compiled by Susumu Nagai (1986)], whereby a transformed yeast pYELF25I/BJ1991 was obtained.

In a similar manner, pYELF25I/BJ1991 and pYELF25V/ BJ1991 were obtained from plasmids pYELF25I and pYELF25V, respectively.

(3) Culturing pYELF25L/BJ1991 obtained above in (2) was cultured at 30° C. for 2 days in 100 ml of YNB/CAA medium, a selective medium, which were placed in a 500 ml Erlenmeyer flask. The culture was centrifuged (3000 rpm, 5 minutes, 20° C.) and the resulting precipitate was suspended in 8.2 ml of YEPD medium.

In a 500 ml Erlenmeyer flask, 2 ml of the suspension (OD550=1.5) was added to 100 ml of YEPD medium, followed by culturing at 30° C. for 2 days.

The transformant containing the plasmid pYELF25I or pYELF25V, that is, pYELF25I/BJ1991 or pYELF25V/ BJ1991 respectively was also cultured by similar procedures.

(4) Purification of elafin derivatives

The above-described culture of pYELEF25L/BJ1991 was centrifuged (8000 rpm, 10 minutes, 4° C.) and the supernatant was filtered (0.22 µm, Falcon Company). After the filtrate was subjected to ultrafiltration ("YM2 Membrane", cut at MW 1000; product of Amicon Corporation), the residue was purified by chromatography on a cation exchange column ("S-Sepharose FF", 1.6×12 cm; product of Pharmacia AB; 40 mM phosphate buffer (pH 6.5), NaCl 0–0.5M gradient).

An active fraction so eluted was purified by reverse phase HPLC ("YMC-AM312"), so that an elafin derivative was obtained.

The elafin derivative so obtained was analyzed by the peptide sequencer ("477A"; manufactured by ABI Inc.). As a result, the sequence from the N-terminal of elafin was confirmed. It was also confirmed that the 25th amino acid residual group from the N-terminal is leucine (see SEQUENCE ID NO: 4 in SEQUENCE LISTING to be described subsequently herein).

From pYELF25V/BJ1991 and pYELF25I/BJ1991, elafin derivatives containing valine as the 25th residual group and isoleucine as the 25th residual group were similarly obtained, respectively (see SEQUENCE ID NO: 6 and 8 in the SEQUENCE LISTING to be described subsequently herein).

Example 2

By modifying the elafin gene of the plasmid pYELF25L through site-directed mutagenesis, a derivative in which the 51th amino acid from the N-terminal, methionine, had been modified was prepared.

Namely, protected oligonucleotides corresponding to the oligonucleotides L51L2 (5'-TGCCAAACCGCAAGAACCTT CGCAGC (SEQ ID NO:15 )) and L51R2 (5'-GCGGTTTGGCATGCTTCGTTCCGCAG (SEQ ID NO.16)) were first chemically synthesized by the DNA synthesizer ("Model 38B"; manufactured by ABI Inc.). After they were deprotected, were purified by polyacrylamide electrophoresis so that oligonucleotides L51L2 and L51R2 were obtained.

Using approximately 10 ng of the plasmid pYELF25L as a template, the above-described primer L51L2 or L51R2 (each 100 pmoles) for site-directed mutagenesis was subjected to a polymerase chain reaction by using Taq polymerase, whereby site-directed mutation was introduced.

Subsequently, in a similar manner to Example 1, pYELF25L51L was prepared. Host cells were transformed by pYELF25L51L. The transformant was then cultured, followed by purification. An elafin derivative in which the 25th and 51st methionines had each been changed to leucine was obtained.

Test 1

Variations (1) in elastase inhibiting activity by oxidation of natural elafin and elafin derivatives Natural elafin and the elafin derivatives were oxidized, and variations in their inhibiting activity against neutrophilic elastase were investigated. Oxidative reaction solutions of natural elafin and the elafin derivatives as elastase inhibitors were each prepared by adding 220 µM of $H_2O_2$ and 6 nM of myeloperoxidase (product of Elastin Products Co., Ltd.) to 250 µl of a phosphate buffer (product of TAKARA SHUZO CO., LTD.) which contained 5 µg of the corresponding elafin or elafin derivative, incubating the resulting mixture at 37° C. for 20 minutes and then adding the same volume of a reaction terminating solution (catalase 0.2 mg/ml, 5 mM methionine).

Further, the measurement of elastase activity was conducted as will be described below by using 5–100 µl of the oxidative reaction solution (inhibitor concentration: 10 µg/ml) of natural elafin and the elafin derivatives prepared as described above.

To 900 µl of a Tris-NaCl buffer (0.1M tris (pH 7.5), 0.5M NaCl, 0.01% $NAN_3$) which contained as a substrate 0.2 mM of methoxysuccinyl-L-alanyl-L-alanyl-L-prolyl-L-valyl-p-nitroanilide (AAPV-pNA; product of Sigma Corporation), 5–100 µl of one of the above oxidative reaction solution and water were added to give 1 ml. Added to the resulting mixture was 0.5 µg of neutrophilic elastase (product of Elastin Products Co., Inc.), followed by incubation at 37° C. for 30 minutes. 0.5 ml of 4N acetic acid was next added to terminate the reaction. Absorbance at 410 nm was measured to determine the elastase activity.

Figure 3:
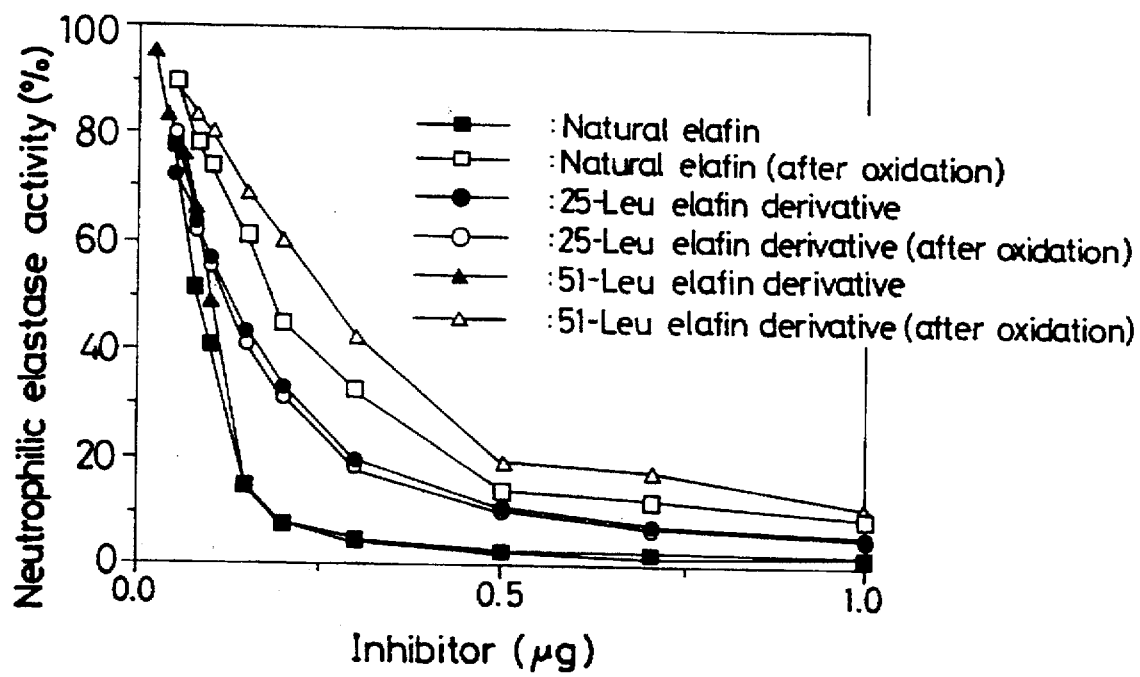
FIG. 3 is a diagram illustrating variations in neutrophilic elastase activity when non-oxidized and oxidized elafins were caused to act as inhibitors, respectively.

The results are shown in FIG. 3. As is evident from the diagram, the elastase inhibiting activity of natural elafin was found to significantly decrease by oxidation. Similar results were observed on the 51st leucine derivative which had not been modified at the 25th site.

In contrast, the elafin derivative according to the present invention in which the 25th methionine had been modified to leucine did not show any oxidation-related reduction in its inhibiting activity against neutrophilic elastase. When compared in oxidized forms, the elafin derivative according to the present invention was clearly found to show stronger inhibiting activity than natural elafin.

Test 2

Variations (2) in elastase inhibiting activity by oxidation of natural elafin and an elafin derivative In a manner similar to Test 1, variations in the pancreatic elastase inhibiting activities of natural elafin and the elafin derivative by oxidation were investigated.

To 1 ml of the Tris-NaCl buffer (0.1M tris (pH 7.5), 0.5M NaCl, 0.01% $NAN_3$) which contained as a substrate 0.2 mM of methoxysuccinyl-L-alanyl-L-alanyl-L-prolyl-L-valyl-p-nitroanilide (AAPV-pNA; product of Sigma corporation), 2–40 µl of one of the oxidative reaction solutions of natural elafin and the elafin derivative, solutions having been prepared in Test 1, were added. Added to the resulting mixture was 0.5 µg of pancreatic elastase (product of Elastin Products Co., Inc.), followed by incubation at 37° C. for 30 minutes. 0.5 ml of 4N acetic acid was next added to terminate the reaction. Absorbance at 410 nm was measured to determine the elastase activity.

Figure 4:
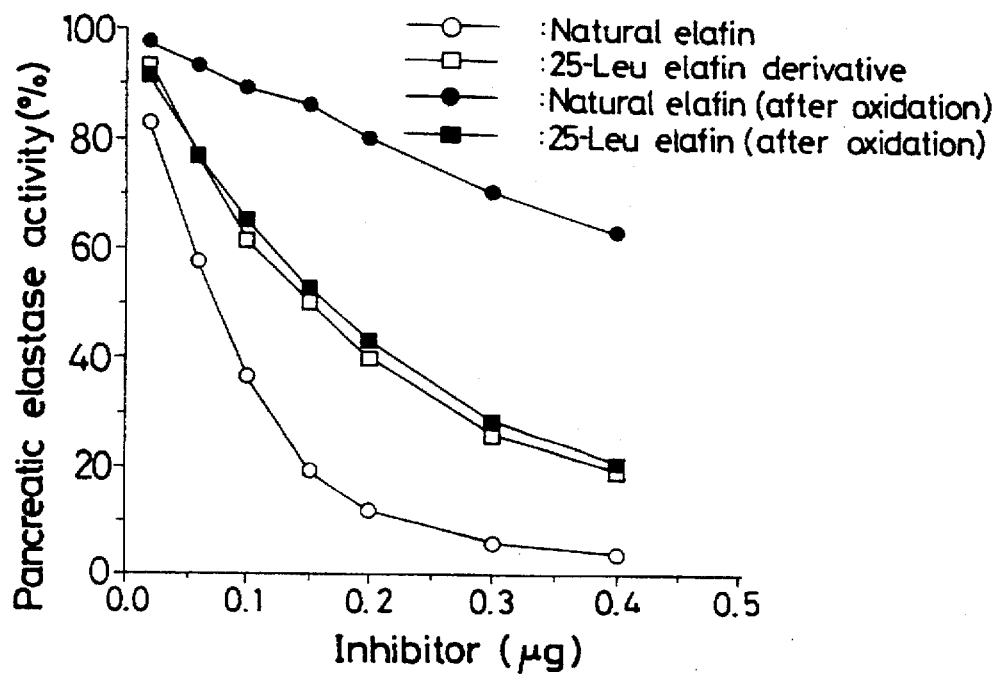
FIG. 4 is a diagram showing variations in pancreatic elastase activity when elafins in a non-oxidized or oxidized form were caused to act, respectively.

The results are shown in FIG. 4. The elafin derivative according to the present invention in which the methionine at the 25th site had been modified to leucine shows absolutely no oxidation-related reduction in its inhibiting activity against pancreatic elastase, so that when compared in the oxidized forms, the elafin derivative according to the present invention was clearly found to show stronger inhibiting activity than natural elafin.

Test 3

Effects of an elafin derivative on the survival rate of endotoxin-treated mice

Using a mouse endotoxin shock model, effects of the elafin derivative according to this invention on the survival rate were investigated while using natural elafin and urinastatin, which is a urinary trypsin inhibitor having anti-elastase action, as comparative substances. After endotoxin was administered at 6 mg/Kg to the caudal veins of ten 7 weeks-old ICR male mice (CHARLES RIVER JAPAN, INC.) in each group, the mice were administered with one of the test substance. Their survival rate was observed along the passage of time. The test substance was administered to the caudal veins of the mice four times in total, that is, 10 minutes before the administration of endotoxin and 3 hours, 6 hours and 12 hours after its administration.

Employed as the test substances were natural elafin, the elafin derivative according to the present invention in which the methionine at the 25th had been modified to leucine (hereinafter called "L-elafin") and urinastatin ("MIRACLID"™;product of MOCHIDA PHARMACEUTICAL CO., LTD.; hereinafter called "UTI").

Natural elafin and L-elafin were each dissolved in a buffer of 20 mM sodium acetate physiological saline, in which 1% bovine serum albumin had been added, whereas UTI was dissolved in the physiological saline.

As a control, a buffer of 20 mM sodium acetate physiological saline, in which 1% bovine serum albumin had been added, was used. The concentrations and doses of the test substances are shown in Table 1.

TABLE 1

| Test substance | Concentration | Volume | Number of administrations (times) | Dose |
|---|---|---|---|---|
| Control | — | 0.1 ml/mouse | 4 | — |
| L-elafin | 0.25 mg/ml | 0.1 ml/mouse | 4 | 0.1 mg/mouse |
| Natural elafin | 0.25 mg/ml | 0.1 ml/mouse | 4 | 0.1 mg/mouse |
| UTI | 5000 I.U./ml | 2.5 ml/Kg | 4 | 50000 I.U./Kg |

Figure 5:
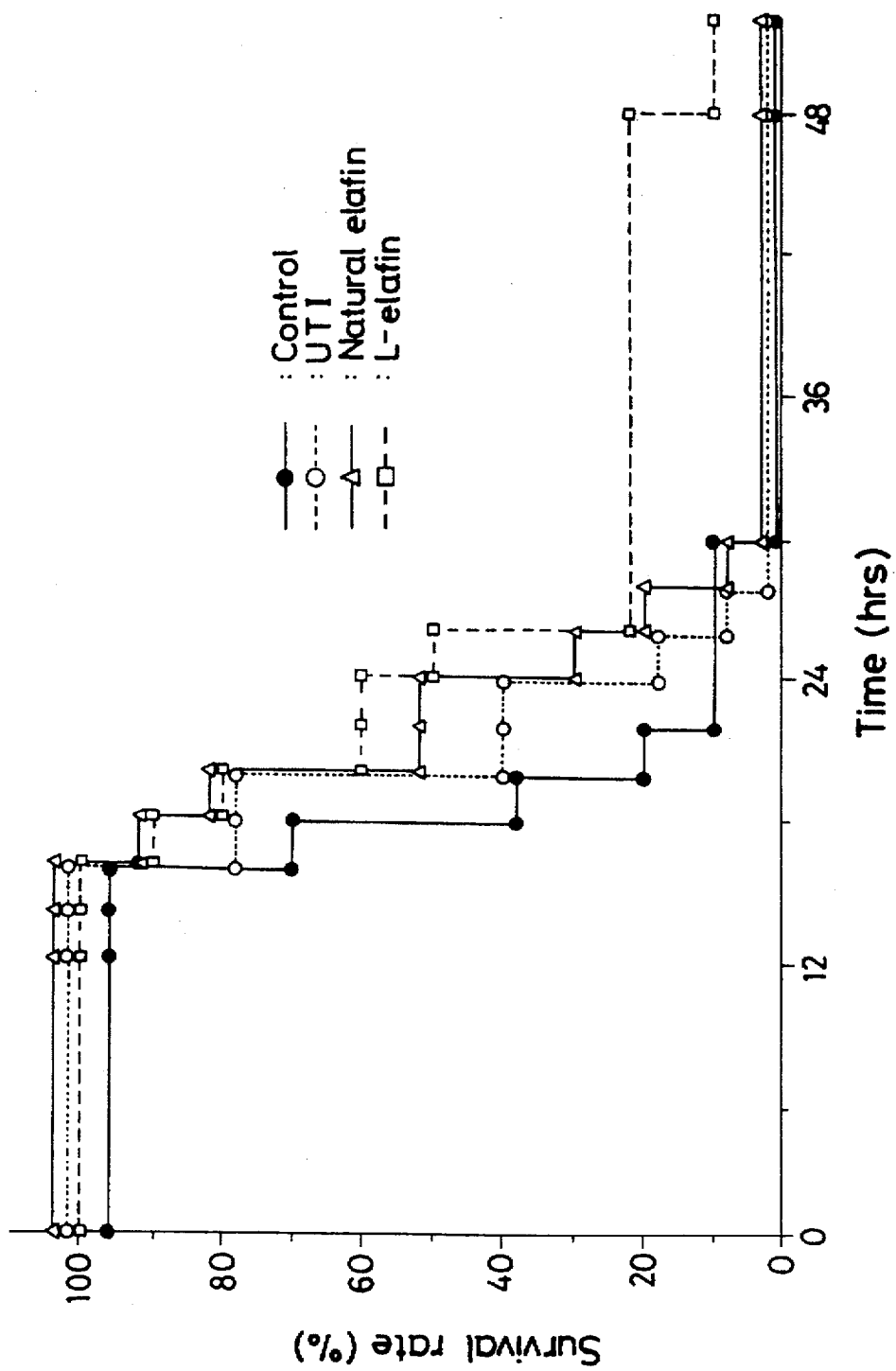
FIG. 5 is a diagram illustrating influence of an elafin derivative according to the present invention, natural elafin and urinastatin on the survival rates of mice administered with endotoxin.

The test results are shown in Table 2 and FIG. 5.

The control group started developing death cases from the 15th hour after the endotoxin administration and the survival rate at 24 hours later was 10%. Further, all the mice had died 31 hours later.

In contrast, the group administered with 0.1 mg/mouse (equivalent to about 3 mg/Kg) of L-elafin showed the tendency to increase the survival rate during 18–24 hours after the administration. 22 hours later, the survival rate was prolonged significantly ($p<0.1$). Although its mechanism of actions is not clear, the elafin derivative according to the present invention seems to specifically inhibit elastase which is produced when shocked, and hence to reduce a septic shock.

TABLE 2

| Test substance (dose) | Survival rate Time after administration of endotoxin (hrs) | | | | | | | | | | | |
|---|---|---|---|---|---|---|---|---|---|---|---|---|
| | 12 | 14 | 16 | 18 | 20 | 22 | 24 | 26 | 28 | 30 | 36 | 48 |
| Control | 10/10 | 10/10 | 7/10 | 4/10 | 2/10 | 1/10 | 1/10 | 1/10 | 1/10 | 1/10 | 0/10 | 0/10 |
| L-elafin (0.1 mg/mouse) | 10/10 | 10/10 | 9/10 | 8/10 | 6/10 | 6/10* | 5/10 | 2/10 | 2/10 | 2/10 | 2/10 | 1/10 |
| Natural elafin (0.1 mg/mouse) | 10/10 | 10/10 | 9/10 | 8/10 | 5/10 | 5/10 | 3/10 | 2/10 | 1/10 | 0/10 | 0/10 | 0/10 |
| UTI (50000 I.U./Kg) | 10/10 | 10/10 | 8/10 | 8/10 | 4/10 | 4/10 | 2/10 | 1/10 | 0/10 | 0/10 | 0/10 | 0/10 |

*$p < 0.01$ vs control

Capability of Exploitation in Industry

The elafin derivatives according to the present invention are stable to oxidation compared with natural elafin and can therefore be used advantageously as drugs such as elastase inhibitors.

We claim:

1. An elafin derivative having the amino acid sequence of SEQ ID NO:1:

Ala Gln Glu Pro Val Lys Gly Pro Val Ser Thr Lys

Pro Gly Ser Cys Pro Ile Ile Leu Ile Arg Cys Ala

Xaa Leu Asn Pro Pro Asn Arg Cys Leu Lys Asp Thr

Asp Cys Pro Gly Ile Lys Lys Cys Cys Glu Gly Ser

Cys Gly Met Ala Cys Phe Val Pro Gln where Xaa is Leu, Ile or Val.

2. An elafin derivative having the amino acid sequence of SEQ ID NO:2:

Ala Gln Glu Pro Val Lys Gly Pro Val Ser Thr Lys
1                   5                    10

Pro Gly Ser Cys Pro Ile Ile Leu Ile Arg Cys Ala
            15                  20

Met Leu Asn Pro Pro Asn Arg Cys Leu Lys Asp Thr
25                  30                   35

Asp Cys Pro Gly Ile Lys Lys Cys Cys Glu Gly Ser
            40                  45

Cys Gly Met Ala Cys Phe Val Pro Gln
        50              55 wherein Met-25 and Met-51 are each, independently, replaced with Leu, Ile or Val, and the derivative has increased stability to oxidation as compared to naturally-occurring elafin.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
      ( A ) LENGTH: 57 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Modified-site
      ( B ) LOCATION: 25
      ( D ) OTHER INFORMATION: /product= "leucine, isoleucine or valine"

( x i ) SEQUENCE DESCRIPTION: SEQ ID NO:1:

| Ala | Gln | Glu | Pro | Val | Lys | Gly | Pro | Val | Ser | Thr | Lys | Pro | Gly | Ser | Cys |
| 1 | | | | 5 | | | | | 10 | | | | | 15 | |

| Pro | Ile | Ile | Leu | Ile | Arg | Cys | Ala | Xaa | Leu | Asn | Pro | Pro | Asn | Arg | Cys |
| | | | 20 | | | | | 25 | | | | | 30 | | |

| Leu | Lys | Asp | Thr | Asp | Cys | Pro | Gly | Ile | Lys | Lys | Cys | Cys | Glu | Gly | Ser |
| | | 35 | | | | | 40 | | | | | 45 | | | |

| Cys | Gly | Met | Ala | Cys | Phe | Val | Pro | Gln |
| | | 50 | | | | 55 | | |

( 2 ) INFORMATION FOR SEQ ID NO:2:

( i ) SEQUENCE CHARACTERISTICS:
        ( A ) LENGTH: 57 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

| Ala | Gln | Glu | Pro | Val | Lys | Gly | Pro | Val | Ser | Thr | Lys | Pro | Gly | Ser | Cys |
| 1 | | | | 5 | | | | | 10 | | | | | 15 | |

| Pro | Ile | Ile | Leu | Ile | Arg | Cys | Ala | Met | Leu | Asn | Pro | Pro | Asn | Arg | Cys |
| | | | 20 | | | | | 25 | | | | | 30 | | |

| Leu | Lys | Asp | Thr | Asp | Cys | Pro | Gly | Ile | Lys | Lys | Cys | Cys | Glu | Gly | Ser |
| | | 35 | | | | | 40 | | | | | 45 | | | |

| Cys | Gly | Met | Ala | Cys | Phe | Val | Pro | Gln |
| | | 50 | | | | 55 | | |

( 2 ) INFORMATION FOR SEQ ID NO:3:

( i ) SEQUENCE CHARACTERISTICS:
        ( A ) LENGTH: 177 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "synthetic DNA"

( i x ) FEATURE:
        ( A ) NAME/KEY: CDS
        ( B ) LOCATION: 1..171

( x i ) SEQUENCE DESCRIPTION: SEQ ID NO:3:

| GCA | CAG | GAA | CCA | GTT | AAA | GGT | CCG | GTG | TCG | ACC | AAA | CCG | GGC | TCT | TGC | 48 |
| Ala | Gln | Glu | Pro | Val | Lys | Gly | Pro | Val | Ser | Thr | Lys | Pro | Gly | Ser | Cys | |
| 1 | | | | 5 | | | | | 10 | | | | | 15 | | |

| CCG | ATT | ATC | CTG | ATC | CGC | TGC | GCT | TTG | CTG | AAC | CCG | CCG | AAC | CGT | TGT | 96 |
| Pro | Ile | Ile | Leu | Ile | Arg | Cys | Ala | Leu | Leu | Asn | Pro | Pro | Asn | Arg | Cys | |
| | | | 20 | | | | | 25 | | | | | 30 | | | |

| CTG | AAA | GAC | ACT | GAC | TGC | CCG | GGT | ATC | AAA | AAA | TGC | TGC | GAA | GGT | TCT | 144 |
| Leu | Lys | Asp | Thr | Asp | Cys | Pro | Gly | Ile | Lys | Lys | Cys | Cys | Glu | Gly | Ser | |
| | | 35 | | | | | 40 | | | | | 45 | | | | |

| TGC | GGT | ATG | GCA | TGC | TTC | GTT | CCG | CAG | TAGTGA | | | | | | | 177 |
| Cys | Gly | Met | Ala | Cys | Phe | Val | Pro | Gln | | | | | | | | |
| | | 50 | | | | 55 | | | | | | | | | | |

( 2 ) INFORMATION FOR SEQ ID NO:4:

( i ) SEQUENCE CHARACTERISTICS:
        ( A ) LENGTH: 57 amino acids
        ( B ) TYPE: amino acid (D) TOPOLOGY: linear (ii) MOLECULE TYPE: protein (xi) SEQUENCE DESCRIPTION: SEQ ID NO:4:

```
Ala Gln Glu Pro Val Lys Gly Pro Val Ser Thr Lys Pro Gly Ser Cys
 1               5                  10                      15

Pro Ile Ile Leu Ile Arg Cys Ala Leu Leu Asn Pro Pro Asn Arg Cys
             20                  25                  30

Leu Lys Asp Thr Asp Cys Pro Gly Ile Lys Lys Cys Cys Glu Gly Ser
         35                  40                  45

Cys Gly Met Ala Cys Phe Val Pro Gln
         50                  55
```

(2) INFORMATION FOR SEQ ID NO:5:

(i) SEQUENCE CHARACTERISTICS:
(A) LENGTH: 177 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic DNA"

(ix) FEATURE:
(A) NAME/KEY: CDS
(B) LOCATION: 1..171

(xi) SEQUENCE DESCRIPTION: SEQ ID NO:5:

```
GCA CAG GAA CCA GTT AAA GGT CCG GTG TCG ACC AAA CCG GGC TCT TGC     48
Ala Gln Glu Pro Val Lys Gly Pro Val Ser Thr Lys Pro Gly Ser Cys
             60                  65                  70

CCG ATT ATC CTG ATC CGC TGC GCT GTC CTG AAC CCG CCG AAC CGT TGT     96
Pro Ile Ile Leu Ile Arg Cys Ala Val Leu Asn Pro Pro Asn Arg Cys
         75                  80                  85

CTG AAA GAC ACT GAC TGC CCG GGT ATC AAA AAA TGC TGC GAA GGT TCT    144
Leu Lys Asp Thr Asp Cys Pro Gly Ile Lys Lys Cys Cys Glu Gly Ser
 90              95                 100                    105

TGC GGT ATG GCA TGC TTC GTT CCG CAG TAGTGA                         177
Cys Gly Met Ala Cys Phe Val Pro Gln
             110
```

(2) INFORMATION FOR SEQ ID NO:6:

(i) SEQUENCE CHARACTERISTICS:
(A) LENGTH: 57 amino acids
(B) TYPE: amino acid
(D) TOPOLOGY: linear (ii) MOLECULE TYPE: protein (xi) SEQUENCE DESCRIPTION: SEQ ID NO:6:

```
Ala Gln Glu Pro Val Lys Gly Pro Val Ser Thr Lys Pro Gly Ser Cys
 1               5                  10                      15

Pro Ile Ile Leu Ile Arg Cys Ala Val Leu Asn Pro Pro Asn Arg Cys
             20                  25                  30

Leu Lys Asp Thr Asp Cys Pro Gly Ile Lys Lys Cys Cys Glu Gly Ser
         35                  40                  45

Cys Gly Met Ala Cys Phe Val Pro Gln
         50                  55
```

(2) INFORMATION FOR SEQ ID NO:7:

(i) SEQUENCE CHARACTERISTICS:

(A) LENGTH: 177 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic DNA"

(ix) FEATURE:
(A) NAME/KEY: CDS
(B) LOCATION: 1..171

(xi) SEQUENCE DESCRIPTION: SEQ ID NO:7:

```
GCA CAG GAA CCA GTT AAA GGT CCG GTG TCG ACC AAA CCG GGC TCT TGC    48
Ala Gln Glu Pro Val Lys Gly Pro Val Ser Thr Lys Pro Gly Ser Cys
         60                  65                  70

CCG ATT ATC CTG ATC CGC TGC GCT ATT CTG AAC CCG CCG AAC CGT TGT    96
Pro Ile Ile Leu Ile Arg Cys Ala Ile Leu Asn Pro Pro Asn Arg Cys
     75                  80                  85

CTG AAA GAC ACT GAC TGC CCG GGT ATC AAA AAA TGC TGC GAA GGT TCT   144
Leu Lys Asp Thr Asp Cys Pro Gly Ile Lys Lys Cys Cys Glu Gly Ser
 90                  95                 100                 105

TGC GGT ATG GCA TGC TTC GTT CCG CAG TAGTGA                         177
Cys Gly Met Ala Cys Phe Val Pro Gln
             110
```

(2) INFORMATION FOR SEQ ID NO:8:

(i) SEQUENCE CHARACTERISTICS:
(A) LENGTH: 57 amino acids
(B) TYPE: amino acid
(D) TOPOLOGY: linear (ii) MOLECULE TYPE: protein (xi) SEQUENCE DESCRIPTION: SEQ ID NO:8:

```
Ala Gln Glu Pro Val Lys Gly Pro Val Ser Thr Lys Pro Gly Ser Cys
 1               5                  10                  15

Pro Ile Ile Leu Ile Arg Cys Ala Ile Leu Asn Pro Pro Asn Arg Cys
             20                  25                  30

Leu Lys Asp Thr Asp Cys Pro Gly Ile Lys Lys Cys Cys Glu Gly Ser
         35                  40                  45

Cys Gly Met Ala Cys Phe Val Pro Gln
     50                  55
```

(2) INFORMATION FOR SEQ ID NO:9:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "primer"

(xi) SEQUENCE DESCRIPTION: SEQ ID NO:9:

TTTTATCCAA GGATACCCCT T                                            21

(2) INFORMATION FOR SEQ ID NO:10:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: other nucleic acid (A) DESCRIPTION: /desc = "primer"

(xi) SEQUENCE DESCRIPTION: SEQ ID NO:10:

CTTGGATAAA AGGGCACAGG AACCAGTTAA AG 32

(2) INFORMATION FOR SEQ ID NO:11:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:11:

GACCTTTAAC TGGTTCCTGT GCCCTTTATC 30

(2) INFORMATION FOR SEQ ID NO:12:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:12:

CGGGTTCAGA ATAGCGCAGC G 21

(2) INFORMATION FOR SEQ ID NO:13:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:13:

CGGGTTCAGG ACAGCGCAGC G 21

(2) INFORMATION FOR SEQ ID NO:14:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:14:

CGGGTTCAGC AAAGCGCAGC G 21

(2) INFORMATION FOR SEQ ID NO:15:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: other nucleic acid (A) DESCRIPTION: /desc = "primer"

(xi) SEQUENCE DESCRIPTION: SEQ ID NO:15:

TGCCAAACCG CAAGAACCTT CGCAGC     26

(2) INFORMATION FOR SEQ ID NO:16:

(i) SEQUENCE CHARACTERISTICS:
  (A) LENGTH: 26 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "primer"

(xi) SEQUENCE DESCRIPTION: SEQ ID NO:16:

GCGGTTTGGC ATGCTTCGTT CCGCAG     26